June 10, 1952 W. S. HAHN Plant Pat. 1,102
IVY PLANT
Filed Sept. 11, 1950
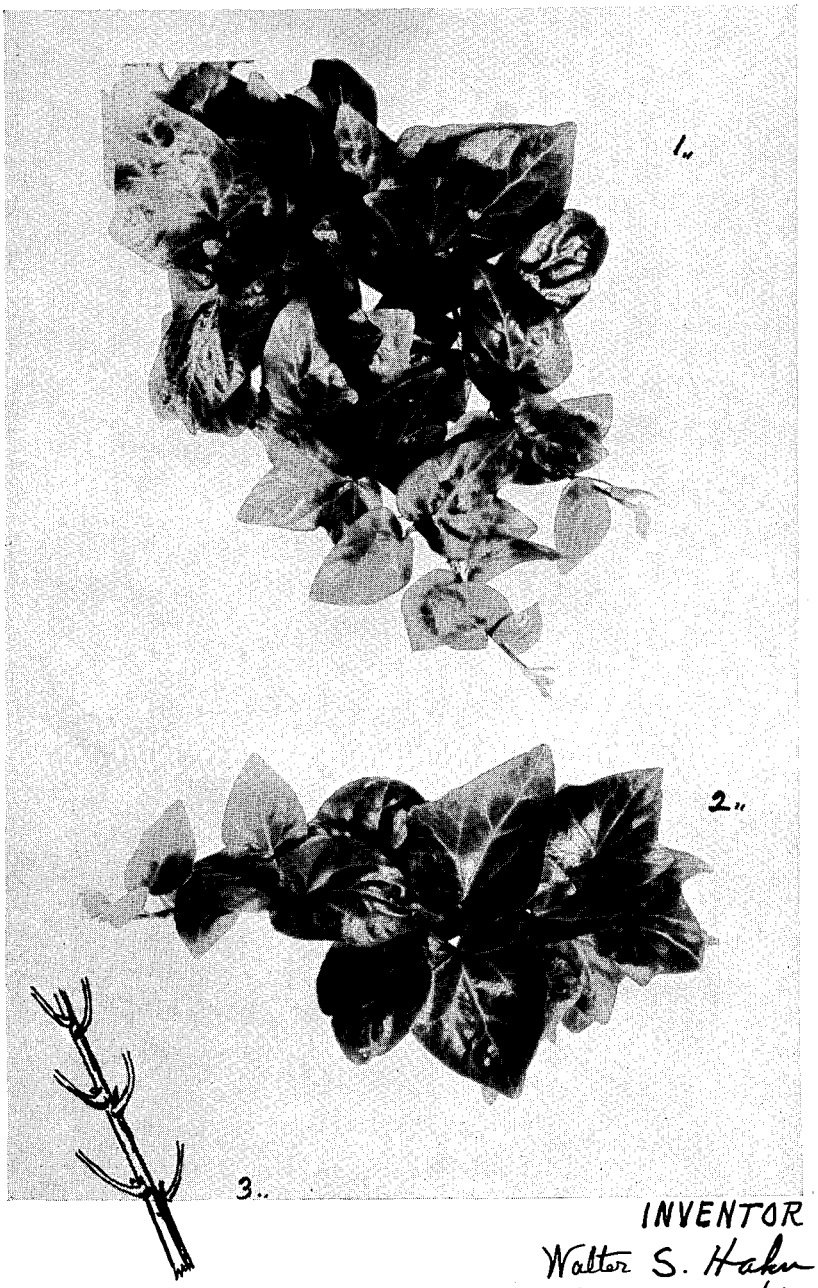
INVENTOR
Walter S. Hahn
By Orville M. Kile
Plant Patent Agt.

Patented June 10, 1952

Plant Pat. 1,102

UNITED STATES PATENT OFFICE 1,102

IVY PLANT

Walter S. Hahn, Pittsburgh, Pa., assignor to
Louis Hahn & Son, Pittsburgh, Pa.

Application September 11, 1950, Serial No. 184,313

1 Claim. (Cl. 47—59)

This new variety of ivy plant was discovered by me in our extensive greenhouses in suburban Pittsburgh, Pennsylvania as a sport of the variety patented by me October 15, 1940, bearing the Plant Patent Number 430. For several years it has been reproduced by me from cuttings. The variety is hardy and grows readily in open fields in the Pittsburgh latitude.

The accompanying photographic illustration shows: (1) a plant 2½ to 3 months of age, grown under average greenhouse conditions, and (2) a single branch to bring out more clearly the size, shape, veination and arrangement of leaves on the petioles and stem, while in the lower left-hand corner the drawing numbered (3) shows diagrammatically the arrangement of the petioles on the central stem, and embryos of additional leaves in the axils.

While having many of the habits of growth and of the desirable qualities of patented ivy No. 430, there are distinct and notable differences both in shape, size, texture and veination of the foliage, and in the general appearance of the plant—the latter due partly to extensive overlapping of the large leaves arranged in pairs almost opposite on the central stems or runners.

This new variety is freely self-branching and a rapid grower, which features produce dense plants large enough to be salable at a very early age. When branches reach an upright height of six to eight inches they fall over and assume a reclining position, or pendulous position if plant is suspended.

The internodes are short and the petiole of each leaf is medium to short. Moreover, the petioles branch from the central stem in pairs, not directly opposite but with such very short internodes between the two as to appear to be in opposite pairs and actually to produce nearly twice as many leaves per inch of stem as in most varieties of ivy known to me. This refers to the number and arrangement of leaves before branching begins. As a particular stem or runner matures, additional leaves develop at many of the axils. Those growth-arrangement characteristics are illustrated in the drawing numbered (3). All of these features, taken together with the large size of the individual leaves, cause an extreme overlapping of leaves, somewhat in imbricated or shingle fashion, that completely conceals the central stem of each branch except at the tips where the new leaves are smaller. As the base of the plant is approached, the branching multiplies the effect of compactness.

Most of the mature leaves are somewhat hastate in form with three lobes. In some cases all three lobes are prominent but other leaves on the same plant will have only one or two lobes. Many leaves tend to be cordate in shape, although all have acute tips. The tendency to form prominent lobes and long sharp terminal points is much less noticeable in this variety than in the parent plant (Plant Patent Number 430).

The average length of the mature leaves is two and one-half to three inches, and the average width is two inches, although of course these dimensions will vary considerably in different positions on the central stem and with different growing conditions. The average size of leaf is considerably larger than that of the parent plant (Plant Patent Number 430), when grown under similar conditions.

The prominent veining of the leaves of this new variety is a feature contributing definitely to its distinctive appearance. While the principal veins are raised (varix), they often appear to be depressed due to the raised surfaces between prominent veins on many of the older leaves, which give these leaves a somewhat crinkled effect in places. The extremely heavy texture of the mature leaves is also a notable feature.

The upper surface of the mature leaves is glossy and somewhat waxy in appearance. The color of foilage and stems is similar to that of the parent plant (Plant Patent Number 430)—namely, dark glossy green in color, from Forest Green (Pl. XXVII) to Dark Dull Yellow Green (Pl. XXXII) on the upper surface and a paler green underneath, from Light Bice Green (Pl. XVII) to Cress Green (Pl. XXXI). The newer leaves are, of course, somewhat lighter than the mature foliage, being approximately Lettuce Green (Pl. V) and very glossy on the upper surface. Leaf petioles are approximately Biscayne Green (Pl. XVII) with slight brownish tinge near stem. Older stems are overlaid with brown approximately Dresden Brown (P.XV), while the newer tips have a slight reddish tinge.

Having thus disclosed my discovery, I claim:

The new and distinct variety of self-branching ivy plant substantially as herein described and illustrated, characterized particularly by its rapid and exceptionally compact growth; the large size and short petioles of its leaves, together with short internodes and arrangement of the leaves in pairs, resulting in dense overlapping; also distinguished by the shape, very heavy texture, prominent veining and somewhat raised and crinkled surface of the older leaves; and its habit of growing to a height of 6 to 8 inches before tending to recline.

WALTER S. HAHN.

REFERENCES CITED

The following references are of record in the file of this patent:

UNITED STATES PATENTS

| Number | Name | Date |
|---|---|---|
| Pl. Pt. 430 | Hahn | Oct. 15, 1940 |